Aug. 13, 1940. N. GRILLO Plant Pat. 417
ROSE
Filed Jan. 21, 1939
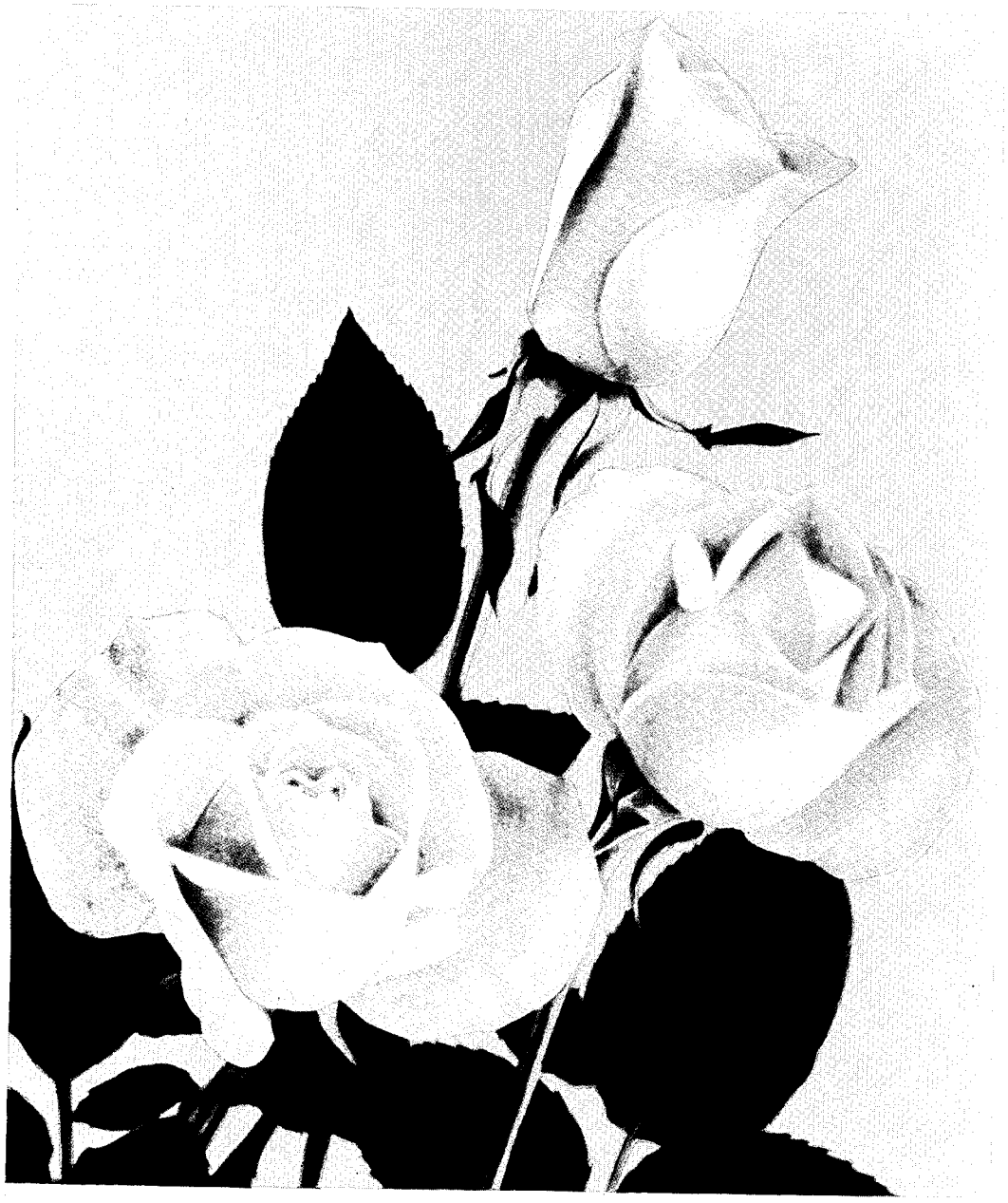
INVENTOR
Nicholas Grillo
By Orville M. Kile
Plant Patent Agent Patented Aug. 13, 1940

UNITED STATES PATENT OFFICE

417

ROSE

Nicholas Grillo, Milldale, Conn.

Application January 21, 1939, Serial No. 252,225

1 Claim. (Cl. 47—61)

My new discovery relates to pink hybrid tea roses and is an improvement over the Briarcliff of which it is a sport. I discovered this new sport several years ago as a branch on a plant of Briarcliff in my greenhouse.

This new variety is similar to its parent in many ways, although it differs in several important points. It is a much deeper pink than Briarcliff and retains its color with little or no fading. The trade has been seeking a rose of the Briarcliff type but with a deeper, more lasting shade of pink and I believe my present variety fills this desire. Added to this is the fact that my new variety has much stronger stems than those of Briarcliff, which gives a more regal and stately appearance to the new rose.

I have asexually reproduced this new variety and find that the distinguishing characteristics are firmly fixed.

The accompanying illustrations show three specimens of this new variety in various stages of opening.

Color plate references are to Ridgway's Color Standards and Nomenclature.

A detailed description of this new variety follows.

*The plant*

Growth: Upright bush. Growth similar to that of Briarcliff but with much stronger stems. More prolific than Briarcliff because the growth breaks from the hard wood as well as from the soft wood.

Foliage: Abundant and of excellent substance.

*Leaves.*—Compound; 3 to 5 leaflets. *Leaflets*—oval with curved acuminate apex and rounded base; margin sharply serrated; surface smooth. *Size*—terminal leaflets average about 3 inches long by 1½ inches wide. *Color*—very dark on the upper surface. The nearest color in Ridgway's is Dusky Yellowish Green (Plate XLI). The under surface, including midrib, is usually tinged with considerable Deep Purple Vinaceous (Plate XLIV), giving the under side of the leaf a purple glow. There is often a hint of purple at the edge of the upper surface. Midribs and petioles usually are purpled on the upper side as well as the under side.

*Rachis.*—Grooved and purpled on upper side. Under side smooth, also purpled.

*Stipules.*—Long; clinging; have long sharp points which frequently are curved and inclined to be foliaceous.

*Stems.*—Long; straight; stout; Cerro Green (Plate V). *Peduncle*—smooth, thorns below first leaf. *Thorns*—large; pinkish; downward-pointing; more numerous on lower part of stem.

*Sepals.*—Long. At least two are inclined to be foliaceous. Leaf-like portion purplish underneath just as the leaves are.

*The flower*

Bud:

*Shape.*—Long; slender; pointed. Later is urn-shape.

*Size.*—Medium.

*Color.*—Almost Rose Color (Plate (XII) although slightly lighter.

Bloom:

*Size.*—Medium, being 4 to 4½ inches across.

*Form.*—High-centered, retaining its form.

*Petalage.*—Averages around 50 petals in September. *Petals*—of good substance. *Shape*—almost round, somewhat ruffled edges, with a single notch at the top of most of the petals. *Color*—the general color effect is uniform, the shade falling between Deep Rose Pink and Rose Color (Plate XII) but with a brilliance not contained in either of the colors mentioned. However, upon closer examination it is found that the inside of each petal has a lighter area at the base. This area is green at the point of attachment, with a small surrounding area of white which merges into the Rose shades at the upper and outer portion of the petal.

*Fragrance.*—Definite but pleasant.

*Lasting qualities.*—Excellent.

*Behavior.*—Retains form and petals cling tenaciously.

*Reproductive organs*

Pistils: Many; bunched; greenish white style; stigma approximately Spinel Pink (Plate XXVI), with greenish white tip.

Stamens: Few; white filament; light yellow anthers approximately Light Cadmium (Plate IV) on the edges with a pinkish tinge on the central portion.

Having thus disclosed my discovery, I claim:

A new variety of hybrid tea rose as shown and described, characterized particularly by its prolific growth; its exceedingly stout stems; its blossoms of lasting, brilliant pink color as described; and its dark green foliage with purplish under surface.

NICHOLAS GRILLO.